US007250303B2

(12) United States Patent
Jakubowicz et al.

(10) Patent No.: US 7,250,303 B2
(45) Date of Patent: Jul. 31, 2007

(54) CHEMISTRY SYSTEM FOR A CLINICAL ANALYZER

(75) Inventors: Raymond Francis Jakubowicz, Rush, NY (US); Michael W. LaCourt, Spencerport, NY (US); David Angelo Tomasso, Rochester, NY (US); James David Shaw, Rochester, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 595 days.

(21) Appl. No.: 10/185,613

(22) Filed: Jun. 28, 2002

(65) Prior Publication Data

US 2003/0022380 A1     Jan. 30, 2003

Related U.S. Application Data

(60) Provisional application No. 60/306,830, filed on Jul. 20, 2001.

(51) Int. Cl.
    *G01N 35/08*     (2006.01)
(52) U.S. Cl. .................... 436/54; 422/100; 422/130
(58) Field of Classification Search ............... 422/100, 422/130; 436/54
    See application file for complete search history.

(56) References Cited

U.S. PATENT DOCUMENTS

| | | | |
|---|---|---|---|
| 3,193,358 A | 7/1965 | Baruch | |
| 3,985,508 A | 10/1976 | Williams | |
| 4,058,252 A | 11/1977 | Williams | |
| 4,155,978 A | 5/1979 | Naono et al. | |
| 4,200,607 A | 4/1980 | Suzuki | |
| 4,260,580 A | 4/1981 | Sindo et al. | |
| 4,305,723 A | 12/1981 | Kolber et al. | |
| 4,310,488 A | 1/1982 | Rahm et al. | |
| 4,325,910 A | 4/1982 | Jordan | |
| 4,338,279 A | 7/1982 | Orimo et al. | |
| 4,452,899 A * | 6/1984 | Alston | 436/46 |
| 4,499,053 A | 2/1985 | Jones | |
| 4,675,162 A | 6/1987 | Sakamaki et al. | |
| 4,678,752 A | 7/1987 | Thorne et al. | |
| 4,708,886 A | 11/1987 | Nelson | |
| 4,708,940 A | 11/1987 | Yoshida et al. | |
| 4,737,342 A | 4/1988 | Herrmann et al. | |
| 4,761,268 A | 8/1988 | Andersen et al. | |
| 4,764,342 A * | 8/1988 | Kelln et al. | 422/72 |
| 4,774,055 A | 9/1988 | Wakatake et al. | |
| 4,808,380 A | 2/1989 | Minekane | |
| 4,844,868 A | 7/1989 | Rokugawa | |
| 4,908,186 A | 3/1990 | Sakamaki | |

(Continued)

FOREIGN PATENT DOCUMENTS

EP     0 073 579 B1     12/1987

(Continued)

*Primary Examiner*—Jill Warden
*Assistant Examiner*—Natalia Levkovich
(74) *Attorney, Agent, or Firm*—Marjama & Bilinski LLP

(57) ABSTRACT

A clinical analyzer for determining the presence or amount of an analyte in a sample includes at least one reagent supply and at least one reaction containment device for containing a volume of sample and a volume of said at least one reagent from said at least one reagent supply. A wash-free delivery system introduces reagent into at least one reaction containment device without requiring washing of delivery components.

23 Claims, 7 Drawing Sheets

U.S. PATENT DOCUMENTS

| | | | |
|---|---|---|---|
| 4,908,320 A | 3/1990 | Zakowski et al. | |
| 4,961,906 A | 10/1990 | Andersen et al. | |
| 5,031,797 A | 7/1991 | Boris et al. | |
| 5,037,612 A | 8/1991 | Takahashi et al. | |
| 5,051,238 A | 9/1991 | Umetsu et al. | |
| 5,055,262 A | 10/1991 | Sakagami | |
| 5,134,079 A | 7/1992 | Cusack et al. | |
| 5,145,646 A | 9/1992 | Tyranski | |
| 5,250,440 A | 10/1993 | Kelln et al. | |
| 5,253,774 A | 10/1993 | Honig et al. | |
| 5,257,650 A | 11/1993 | Fisk et al. | |
| 5,264,182 A | 11/1993 | Sakagami | |
| 5,282,149 A | 1/1994 | Grandone et al. | |
| 5,289,385 A | 2/1994 | Grandone | |
| 5,294,404 A | 3/1994 | Grandone et al. | |
| 5,296,195 A | 3/1994 | Pang et al. | |
| 5,314,825 A | 5/1994 | Weyrauch et al. | |
| 5,357,095 A | 10/1994 | Weyrauch et al. | |
| 5,358,691 A | 10/1994 | Clark et al. | |
| 5,369,566 A | 11/1994 | Pfost et al. | |
| 5,374,395 A | 12/1994 | Robinson et al. | |
| 5,482,861 A | 1/1996 | Clark et al. | |
| 5,501,982 A | 3/1996 | Saldivar, Jr. et al. | |
| 5,508,200 A | 4/1996 | Tiffany et al. | |
| 5,540,890 A | 7/1996 | Clark et al. | |
| 5,576,215 A | 11/1996 | Burns et al. | |
| 5,582,796 A | 12/1996 | Carey et al. | |
| 5,585,068 A * | 12/1996 | Panetz et al. | 422/64 |
| 5,610,069 A | 3/1997 | Clark et al. | |
| 5,637,275 A | 6/1997 | Carey et al. | |
| 5,670,114 A | 9/1997 | Sakazume et al. | |
| 5,670,120 A | 9/1997 | Degenhardt et al. | |
| 5,679,309 A | 10/1997 | Bell | |
| 5,730,938 A | 3/1998 | Carbonari et al. | |
| 5,746,977 A | 5/1998 | Imai et al. | |
| 5,776,784 A | 7/1998 | Kegelman et al. | |
| 5,789,252 A | 8/1998 | Fujita et al. | |
| 5,807,523 A | 9/1998 | Watts et al. | |
| 5,846,492 A | 12/1998 | Jacobs et al. | |
| 5,856,194 A | 1/1999 | Arnquist et al. | |
| 5,885,529 A | 3/1999 | Babson et al. | |
| 5,885,530 A | 3/1999 | Babson et al. | |
| 5,902,549 A | 5/1999 | Mimura et al. | |
| 5,985,672 A | 11/1999 | Kegelman et al. | |
| 6,027,691 A | 2/2000 | Watts et al. | |
| 6,143,252 A * | 11/2000 | Haxo et al. | 422/131 |
| 6,551,558 B1 * | 4/2003 | Mann et al. | 422/100 |
| 6,797,518 B1 | 9/2004 | Jacobs et al. | |
| 2001/0019826 A1 * | 9/2001 | Ammann | 435/6 |
| 2002/0110487 A1 | 8/2002 | Samsoondar | |
| 2005/0054112 A1 | 3/2005 | Jacobs et al. | |

FOREIGN PATENT DOCUMENTS

| | | |
|---|---|---|
| EP | 0 336 309 A3 | 3/1989 |
| EP | 0 195 893 B1 | 6/1989 |
| EP | 0 331 057 | 9/1989 |
| EP | 0 336 309 A2 | 10/1989 |
| EP | 0 274 519 B1 | 1/1993 |
| EP | 0 576 291 A2 | 12/1993 |
| EP | 0 712 000 B1 | 5/1996 |
| EP | 0 504 313 B1 | 6/1997 |
| EP | 0 889 328 A1 | 1/1999 |
| EP | 0 930 495 A1 | 7/1999 |
| EP | 0 945 728 A2 | 9/1999 |
| EP | 0 949 506 A2 | 10/1999 |
| EP | 0 984 284 A2 | 3/2000 |
| JP | 61-290634 | 12/1986 |
| JP | 02-269972 | 11/1990 |
| JP | 04-359154 | 12/1992 |
| JP | 09-127127 | 5/1997 |
| JP | 10-123136 | 5/1998 |
| JP | 2000-137036 | 5/2000 |
| WO | WO 87/06008 | 10/1987 |
| WO | WO 92/20778 A1 | 11/1992 |
| WO | 93/20440 | 10/1993 |
| WO | 93/20444 | 10/1993 |
| WO | WO 93/20441 | 10/1993 |
| WO | 93/22686 | 11/1993 |
| WO | 96/23219 | 8/1996 |
| WO | 97/22006 | 6/1997 |
| WO | 98/00697 | 1/1998 |
| WO | WO 99/47261 A1 | 9/1999 |

\* cited by examiner

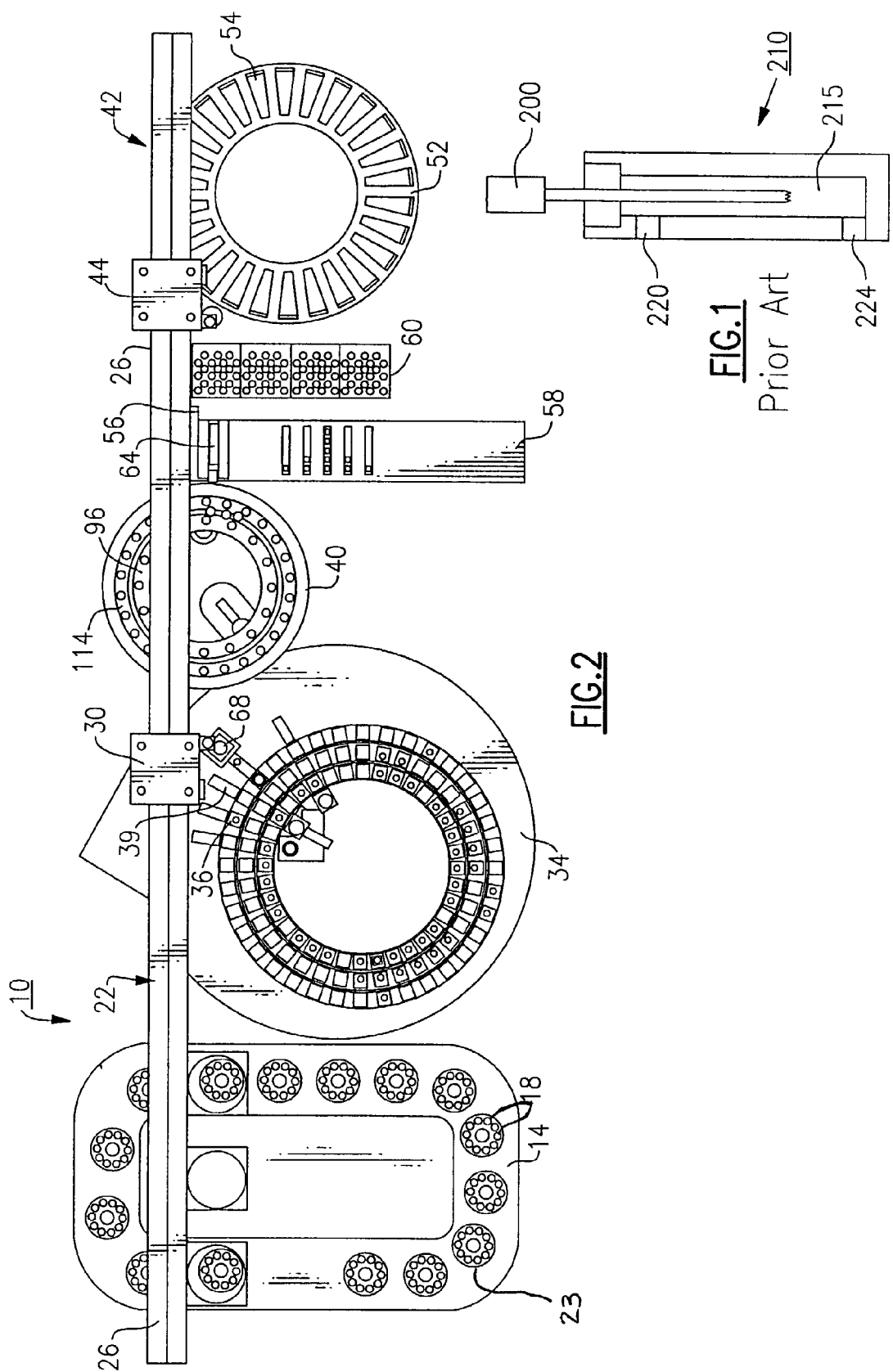

CHEMISTRY SYSTEM FOR A CLINICAL ANALYZER

CROSS REFERENCE TO RELATED APPLICATION

Reference is made to and priority claimed from U.S. provisional application Ser. No. 60/306,830 filed Jul. 20, 2001, entitled CHEMISTRY SYSTEM FOR A CLINICAL ANALYZER.

FIELD OF THE INVENTION

The invention relates to the field of analytical sample measurement and more particularly to a chemistry system for a clinical blood analyzer which does not require wash operations between fluid delivery events in the preparation and conduction of wet or dry assays.

BACKGROUND OF THE INVENTION

Clinical analysis systems or analyzers having so-called "wet" chemistry systems require a sample supply for retaining a plurality of patient sample containers, at least one reagent supply containing at least one reagent, and at least one reaction containment device to carry out a wet assay. The reaction containment device can assume many different forms, but typically the device is either a cuvette containing a plurality of reaction chambers or a single reaction well. The assay is incubated during the formation thereof on an aliquot of sample which is combined, depending on the assay, with certain other fluids, such as reagents, and/or other substances to create some noticeable event, such as fluorescence or light absorbency. The event can subsequently be measured using a testing device, such as a spectrophotometer, colorimeter, reflectometer, electrometer, polarimeter, luminometer or other suitable device in order to detect the event and perform correlated analyte detection.

In chemistry systems of this type and particularly with immunoassays, multiple reagents and washing steps are required to prevent carryover. That is, whenever reagent metering involves aspirating and dispensing of different reagents, it is desirable to include at least one wash step so that the reagent metering probe does not carry over reagent from one step of an assay into a different step of an assay or into a different assay.

In general, a reagent probe is used to aspirate a quantity of reagent from a reagent supply, and then dispense the reagent into the reaction vessel. Following dispensing and prior to aspirating a new reagent, the probe must then be washed to avoid carryover. By "washing", what is meant is that the reagent probe must be flushed with a wash fluid after delivery of each reagent component. The reagent probe is fluidly interconnected to a wash solution wherein the probe can be charged and dispense wash fluid by vacuum or pressure. The reagent wash station includes a wash cylinder which provides an enclosed space for the probe in order to conduct a wash step. In operation, the probe is lowered by conventional means into the wash cylinder of the wash station and wash fluid is charged through the probe and into the wash cylinder and evacuated through an outlet port. The wash fluid is also charged through an inlet port in order to wash the exterior of the probe.

The wash operation further requires the use of a fluid (wash) supply and associated tubing and pneumatic or other fluid delivery apparatus in order to direct wash fluid from the supply into the wash station. Similarly, waste wash fluid must be collected from the wash station and is directed through similar pneumatics or similar fluid delivery means to a waste supply. Typically, each of the wash supply and the waste supply are contained in bottle-like containers that are typically located in a lower cabinet of the analyzer housing.

A known example of the above form of analyzer is now more specifically described. In brief, the analyzer includes a housing having a set of reagent wells which are stacked in combination with a reagent supply containing a reagent. The reagent wells can be accessed selectively for test assays to be conducted.

Initially and according to the analyzer described herein, an empty reaction well is removed from a well supply and transferred into an incubator. The empty reaction well is shifted by known means of the incubator to a sample metering station within the incubator to receive metered sample. A conical metering tip located at a tip supply is collected by a metering mechanism, the conical tip being applied or otherwise attached to the end of a proboscis. Following attachment, the tip is transferred from the tip supply on a pivotal or linear metering arm retaining the proboscis to a primary sample supply having a plurality of primary tubular sample containers. The proboscis having the attached metering tip is lowered into a designated primary sample container and a volume of patient sample is aspirated into the tip. The tip is then raised from the primary patient container and the metering arm is moved to the sample metering position at the incubator. The tip is lowered into an opening provided in the incubator cover defining the sample metering station and sample is dispensed into the reaction well. Following the above metering step, the used metering tip is stripped from the proboscis and is discarded at a dump station.

The reaction well is then further incubated within the incubator to a reagent metering position. In this position, the reagent probe is brought to a first reagent container and a volume of reagent fluid is aspirated from the container into the probe. The probe is then pivoted to the incubator, lowered into the reagent metering position, and dispenses the reagent into the reaction well. The probe is not placed into contact with the sample fluid already contained within the reaction well. Rather, the reagent is injected at high velocity into the reaction well to induce mixing. In addition, the incubator includes a vibratory bed which further promotes mixing to occur.

The reagent probe is then raised from the incubator and pivoted to a wash station, such as shown in FIG. 1. As previously noted, the wash station 210 includes a wash cylinder 215 which provides an enclosed space and into which the reagent probe 200 is positioned. Wash liquid from a wash liquid supply (not shown) is charged both into the interior of the reagent probe 200 and along the exterior of the reagent probe 200 through an inlet port 220 by means of an elaborate pneumatic system (not shown) having at least one pump as well as sufficient valving and tubing for fluidly directing wash liquid from the wash liquid supply. Waste liquid is directed through the contents of the reagent probe 200 to an outlet port 224 and subsequently by means of a separate pneumatic/fluidic system (not shown) to a waste chamber (not shown) provided at the bottom of the analyzer housing in a dedicated cabinet (not shown).

Depending on the assay, the reaction well is then further incremented within the incubator to a second reagent metering position. At this position, the reagent probe is shuttled to the second reagent supply and a suitable volume of second reagent is aspirated into the probe for dispensing into the reaction well. As in the preceding, fluid from the probe is injected into the reaction well in order to promote mixing of the contents. Following this dispensing step, the reaction probe is again positioned by the metering system to the wash station and the preceding wash steps are repeated. Additional reagents can be added, again depending on the type of assay.

The sample fluid and reagents are then incubated together. In the example herein described, the reaction well may include a bonded antibody layer. If luminescent tests are required for the assay, the contents of the reaction well must first be washed in order to remove the fluid contents through a series of washing and suction steps. The remaining bound material then receives a signal generating reagent prior to testing using a luminometer. Chemiluminescent signals generated by the reagent/sample combination are transmitted to a photo multiplier which converts the light signal into an electrical signal for processing according to conventional digital techniques. The signal generating agent is dispensed using the reagent probe as previously described or pumped directly from bottles. The reagent probe is washed following dispensing of the reagent to the reaction well.

Alternately, and if light absorbency testing is required, then the reagent/sample fluid combination contained in the reaction well is tested using an optical testing device, such as a spectrophotometer. Additional details relating to the wash-related steps and the preparation of assays using the above analyzer are provided in commonly assigned and co-pending U.S. application Ser. No. 09/482,599, entitled: FAILURE DETECTION IN AUTOMATED CLINICAL ANALYZERS, the entire contents of which are incorporated by reference.

It should be further noted that additional problems in addition to those relating to the overall cost and complexity of providing wash apparatus to a clinical analyzer include potential risks of cross contamination of fluids, particularly reagents given that reagent packs can include multiple adjacent bottles, each bottle having a different reagent.

There is a generally recognized need in the field to eliminate or substantially reduce the complexity of clinical analytical systems in which assays, such as described above, are conducted.

SUMMARY OF THE INVENTION

It is a primary object of the present invention to overcome the above-noted deficiencies of the prior art.

It is another primary object of the present invention to eliminate the expense and complexity created by wash-related apparatus and processes which mainly accompany a wet chemistry system for a clinical analyzer.

Therefore and according to a preferred aspect of the present invention, there is provided a wash-free reagent delivery system for introducing a volume of at least one reagent into a reaction containment device in a clinical analyzer, said system including:

at least one reagent supply; and reagent wash-free delivery means for introducing a volume of at least one reagent from said at least one reagent supply to at least one reaction containment device.

Preferably, and according to one embodiment, the wash-free delivery means includes a plurality of disposable fluid dispensing elements, such as plastic molded metering tips, which are used to aspirate and dispense reagent into the reaction containment device, such as a cuvette or reaction well. The disposable tips are used to deliver reagent and other liquids to the reaction device and to mix the liquids which are dispensed. According to a preferred embodiment, a single disposable tip is used to aspirate a volume of reagent from the reagent supply and dispense the aspirated reagent into the reaction containment device. Following the dispensing step, the tip is preferably deposited into a dump station. That is to say, each tip is singly or can be multiply used for a fluidic event in the preparation and conduction of an assay. According to another preferred embodiment, the analyzer includes an auxiliary sample holder which retains a plurality of sealable metering tips, wherein the dispense ends of the tips are sealed to retain a volumetric quantity of patient sample. Smaller disposable tips, such as those described above used for reagent metering, are sized to fit within the confines of the sample containing tip, and can therefore be singly utilized, as described above, to aspirate sample fluid from the sealed tips for dispensing into a reaction containment device. The auxiliary sample holder further retains a plurality of unsealed metering tips that can be used alternatively, for example, with the smaller disposable tips for aspirating and dispensing reagent from at least one reagent container. As such, a completely wash-free delivery system for a wet chemistry analyzer is provided. The disposable tips effectively replace the wash plumbing normally associated with a so-called "wet" analyzer.

According to another preferred embodiment, the wash-free delivery means includes at least one reagent container having a dedicated reagent dispensing member which is preferably retained with the container. Preferably, the dedicated fluid dispensing member is a metering tip used solely in conjunction with the reagent container for aspirating and dispensing a contained reagent into at least one reaction vessel. The tip can be picked up by a proboscis, probe, or other metering apparatus as needed and shuttled between a metering station, the reagent container, and a storage location. A single tip can therefore be used in conjunction with the preparation of a multiple number of assays after which the tip can be discarded along with a fully used reagent container. Alternately, the reagent dispensing member can be recycled.

According to yet another preferred embodiment, the wash-free delivery means can include a reagent container having self-dispensing means for dispensing a predetermined amount of reagent into a reaction containment device, such as a reaction cuvette. The self-dispensing means can include for example, a pump mechanism capable of precisely and repeatably delivering a micro volume of reagent upon demand. According to another preferred embodiment, the reagent container can include an actuator mechanism for delivering the predetermined amount of reagent. The reagent container containing the self-dispensing means can be positioned in a dedicated location specifically aligned with a metering position relative to the reaction containment device prior to dispensing liquid therein or the container can be pivotally or otherwise movable therewith.

According to yet another preferred aspect of the invention, there is provided a clinical analyzer for determining the presence or amount of an analyte in a sample, said analyzer comprising:

at least one reagent supply;

at least one reaction containment device for containing a volume of sample and a volume of said at least one reagent from said at least one reagent supply; and wash-free delivery means for introducing said reagent into said at least one reaction containment device without requiring washing thereof.

Preferably though not necessarily, the wash-free delivery means introduces both sample and reagent into the reaction containment device, though the sample wash-free delivery means can be separately distinct from the reagent sample delivery means. Additionally, a reaction containment device can be provided which also does not require washing. For example, the containment device can be disposable.

According to another preferred aspect of the present invention, there is provided a clinical analyzer for determining the presence or amount of an analyte in a sample, said analyzer comprising:

at least one sample supply;

at least one reagent supply;

at least one reaction containment device for containing a volume of sample from said at least one sample supply and a volume of reagent from said at least one reagent supply; and reagent wash-free delivery means for introducing said volume of at least one reagent from said at least one reagent supply into said reaction containment device.

Preferably, the analyzer includes sample delivery means for introducing sample from the at least one sample supply into the reaction containment device. The sample delivery means can also include means for delivering multiple quantities of sample without requiring washing thereof.

According to still another preferred aspect of the present invention, there is provided a method for determining the amount or presence of an analyte in a sample using a clinical analyzer, said method including the steps of:

delivering a volume of sample to a reaction containment device;

delivering a volume of at least one reagent from a reagent supply to said reaction containment device using wash-free delivery means for introducing said at least one reagent to said reaction containment device thereby forming a detectable species in said containment device; and determining the formed species.

Preferably, the sample delivering step includes the steps of aspirating a volume of sample from a sample supply into a fluid dispensing member and dispensing aspirated sample into the reaction containment device using the dispensing member. The dispensing member is then discarded following the above dispensing step; that is, the dispensing member is utilized for a single fluid delivery event.

The reagent delivering step can include the steps of aspirating a volume of a first reagent from the reagent supply into a first fluid dispensing member, dispensing the reagent into a reaction containment device, discarding the first fluid dispensing member, aspirating a second volume of reagent into a second fluid dispensing element, and dispensing the reagent into the reaction containment device. As such, the fluid dispensing elements effectively replace the wash operations typically required for reagent metering apparatus. Preferably, the dispensing members can be used to dispense different reagents and sample using a common metering system.

According to still another preferred aspect of the invention, there is provided a method for conducting at least one assay in a clinical analyzer, said method including the steps of:

i delivering a volume of sample into at least one reaction containment device;

ii delivering a volume of at least one reagent from a reagent supply into said reaction containment device; and iii repeating at least one of steps i) and ii) wherein a washing operation is not required between any of said delivering steps.

An advantageous feature of the herein described method is that the overall complexity of a wet chemistry system is effectively reduced due to elimination of wash operations normally associated therewith. As a result, an analyzer incorporating the present invention can be manufactured at a lower cost and with a smaller footprint without sacrifice to efficiency, efficacy or safety.

Another advantage of the present invention is that the absence of wash steps provides a significant increase in overall throughput for an analyzer incorporating the herein described "wash-free" system.

Another advantage of the present invention is that the use of disposable tips for "wet" metering permits improved error detection.

Yet another advantage of the present invention is significantly less complex, requiring less maintenance than previously known wash systems, but with improved reliability.

Yet another advantage of the present invention is that a decreased risk of contaminated wash solution. In addition, the present chemistry system eliminates the need to prepare and store wash fluids and eliminates disposable waste liquid.

These and other objects, features, and advantages will be apparent from the following Detailed Description which should be read in conjunction with the accompanying drawings.

BRIEF DESCRIPTION OF THE DRAWINGS

FIG. 1 is a partial elevational view of a wash station of a known clinical analyzer;

FIG. 2 is a top perspective view of a clinical analyzer made in accordance with an embodiment of the present invention;

DETAILED DESCRIPTION

Figure 3:
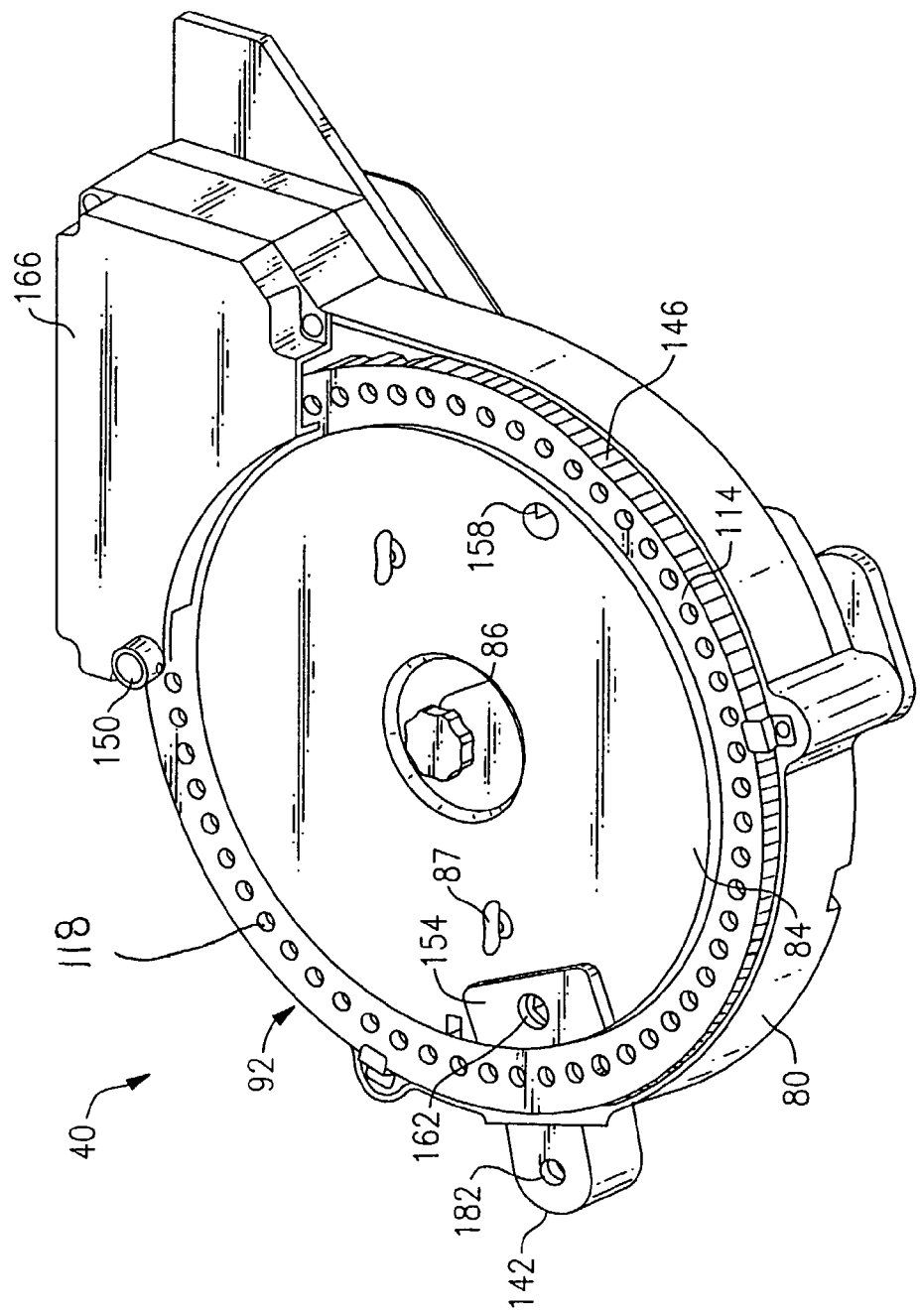
FIG. 3 is a top perspective view of an auxiliary sample handler of the clinical analyzer of FIG. 2.

The following description relates to several embodiments which eliminate wash-related operations in connection with a mainframe, desktop, or other form of clinical analyzer used to measure patient blood samples and sera.

The invention relates in general to wash-free delivery of reagent and other liquids relative to at least one reaction containment device. For purposes of the discussion which follows, "wash-free" is meant to refer to the use of a wash fluid for purposes of cleaning a probe, proboscis, or other delivery apparatus, including the reaction containment device (cuvette, etc), between fluid (patient, reagent, diluent, calibration, etc) delivery operations. Furthermore, this term is intended to encompass the conduction and preparation of both wet and dry assays, excluding only those involving solely dilutions of reagent or sample.

It should be noted, that by "combinational" it is meant that the analyzer includes more than one chemistry system for determining the presence or amount of an analyte in a patient sample. In the present instance, the analyzer 10 includes both a "wet" and a "dry" chemistry system. It will be apparent, however, from the following discussion that the present invention is preferably used in connection with a clinical analyzer having at least one wet chemistry system.

Referring to FIG. 2, there is shown an automated combinational clinical analyzer 10 having a number of component systems. In brief, the analyzer 10 includes a primary sample handler 14 that retains a plurality of primary sample containers 18, a primary metering mechanism 22 which includes a metering transport rail 26 and a metering truck 30 which is movable along the transport rail between a number of stations. Among the stations disposed along the travel path of the metering mechanism 22 are a metering station 68 for a first incubator assembly 34. At the metering station 68, a quantity of sample can be deposited onto a dry slide element 36 which is then shuttled into the first incubator assembly 34. The first incubator assembly 34 includes at least one read station (not shown) including a testing device for correlated analyte detection, such as reflectometer or an electrometer. An auxiliary sample handling apparatus 40, disposed in relation to the first incubator assembly 34, includes a tip supply for maintaining a plurality of metering tips 102, FIGS. 6, 10 and serves to further retain a plurality of secondary sample containers, as described in greater detail below. The preceding components each comprise the "dry" chemistry system for the herein described automated combinational analyzer 10.

Still referring to FIG. 2, the analyzer 10 further includes a secondary metering mechanism 42 that includes a metering truck 44, similar to the movable truck 30 for the dry chemistry portion of the analyzer, which is also movable along the metering transport rail 26, a reagent wheel 52 which includes a plurality of containers of at least one reagent, a second incubator assembly 56, a micro-tip supply 60, and a reaction vessel conveyor 58 which carries a plurality of reaction vessels 64. For purposes of this description, however, each of the above-noted components including the above-referred to auxiliary sample handling apparatus 40 define the "wet" chemistry system for the herein described combinational analyzer 10. As will be evident from the following discussion, the above-described auxiliary sample handler 40 asynchronously links the dry chemistry and wet chemistry systems of the combinational clinical analyzer 10. A more detailed description is now provided regarding the contained components of the analyzer 10.

Referring back to FIG. 2, the sample containers 18 are generally tubular in shape and are disposed on rotatable sample trays 23 disposed on a drive belt or other support. The sample trays 23 are typically carousels which retain a plurality of the tubular sample containers 18, the trays being incremented about an elliptically shaped track by means of a drive mechanism (not shown) such as a magnetic drive, belt or other known means into alignment with the metering transport rail 26. It will be readily apparent that the form of drive mechanisms for the primary sample handler 14 are not in and of themselves essential to the workings of the present invention. A bar code reader (not shown) scans identification data from each patient container 18. Further details regarding typical sample handling apparatus can be found in previously incorporated U.S. patent application Ser. No. 09/482,599.

The metering transport rail 26 is a horizontally disposed beam-like member which substantially spans the length of the analyzer 10 and is used according to this embodiment for both the wet and dry chemistry systems. The metering transport rail 26 as stated above is aligned with the primary sample handler 14 as well as the first incubator assembly 34 and the auxiliary sample handling apparatus 40. The movable truck 30 is a carriage which includes a proboscis (not shown) that is capable of vertical movement so as to permit the proboscis to be selectively raised or lowered relative to a base by means of an appropriate vertical drive mechanism (not shown). A second horizontal drive mechanism (also not shown) permits the truck 30 to move longitudinally along the transport rail 26. Details relating to the drive mechanisms, the metering rail, and the metering transport rail are generally known by those of sufficient skill in the field.

Figure 6:
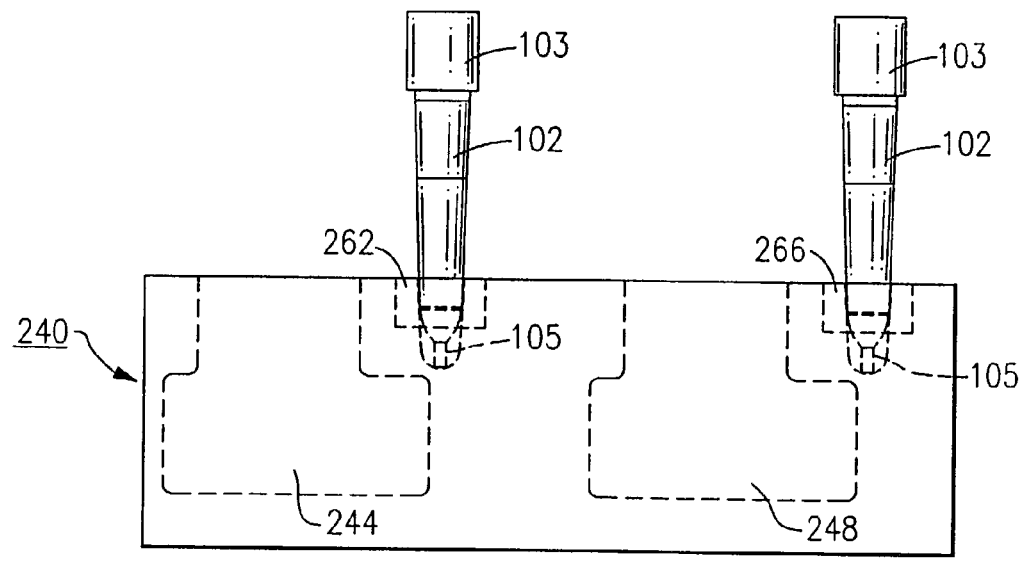
FIG. 6 is a side elevational view of the reagent container of FIG. 5.
Figure 10:
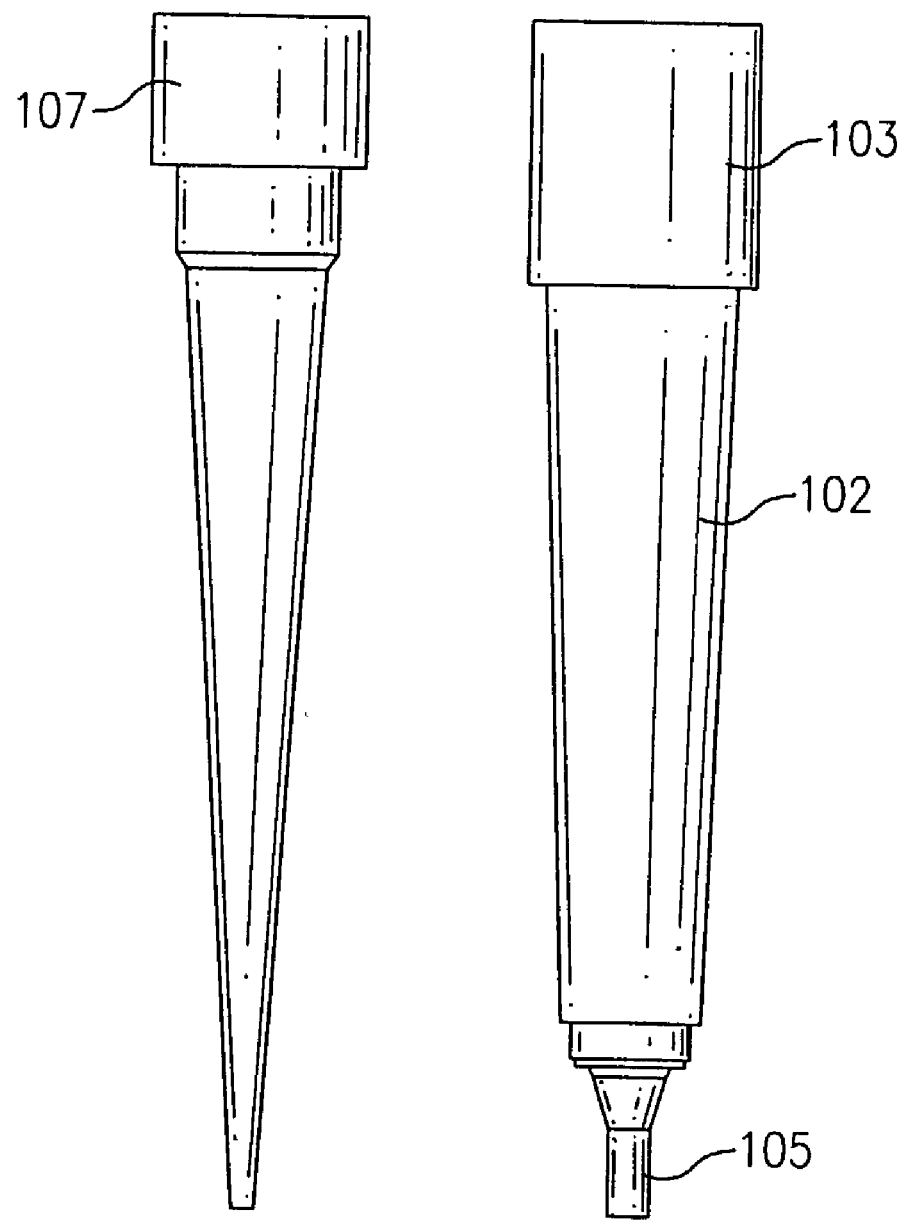
FIG. 10 is a side elevational view of a pair of disposable metering tips used in conjunction with the chemistry system of FIG. 9.

A metering tip 102, FIGS. 6 and 10, is releasably attached or otherwise applied to the proboscis in order to aspirate sample liquid from a primary sample container 18. A plurality of metering tips 102, such as those shown in FIGS. 6, 10, are provided on an outer ring of the auxiliary sample handling apparatus 40, each of the tips including a tapered conical body having a capillary tip which serves as a dispense end 105. Typically, each of the metering tips are made from a molded plastic material which is disposable and which can be removably attached to the end of the proboscis in a commonly known manner.

The metering system 22 further includes a metering pump (not shown) operatively connected to the movable truck 30 and more particularly to the proboscis which can selectively draw various amounts of partial pressure and partial vacuum in order to aspirate liquid into the tip and to dispense liquid from the tip. Additional details regarding the above elements of a metering system are known, for example, in U.S. Pat. No. 4,340,390, the entire contents of which are herein incorporated by reference.

As noted above, and after a predetermined quantity of sample has been aspirated from one of the sample containers 18 into a metering tip 102, FIGS. 6 and 10, the movable truck 30 is transferred by the appropriate drive mechanism to the metering station 68 in order to dispense a predetermined volume of sample fluid from the metering tip 102 onto a thin film or dry slide element 36, such as those described in U.S. Pat. No. 3,992,158 to Przybylowicz, the entire contents of which are herein incorporated by reference. The dry slide elements 36 are sequentially supplied to the metering station 68 via a cartridge (not shown) and following the metering of a portion of contained sample liquid from a metering tip 102, each slide element 36 is shuttled by means of a reciprocating pusher blade 39 or other suitable means into the first incubator assembly 34 for incubating and testing of the sample.

The first incubator assembly 34 according to the present embodiment retains a plurality of spotted slide elements on a multi-ring rotor assembly, the slide elements being driven rotatably about a common axis relative to at least one read station including a testing device such as a reflectometer or electrometer for determining the presence or amount of analyte in a sample. Details relating to dry slide elements and incubator assemblies are commonly known in the field, such as described in U.S. Pat. No. 4,296,069, and therefore require no further discussion, except as required in order to properly understand the invention.

Figure 4:
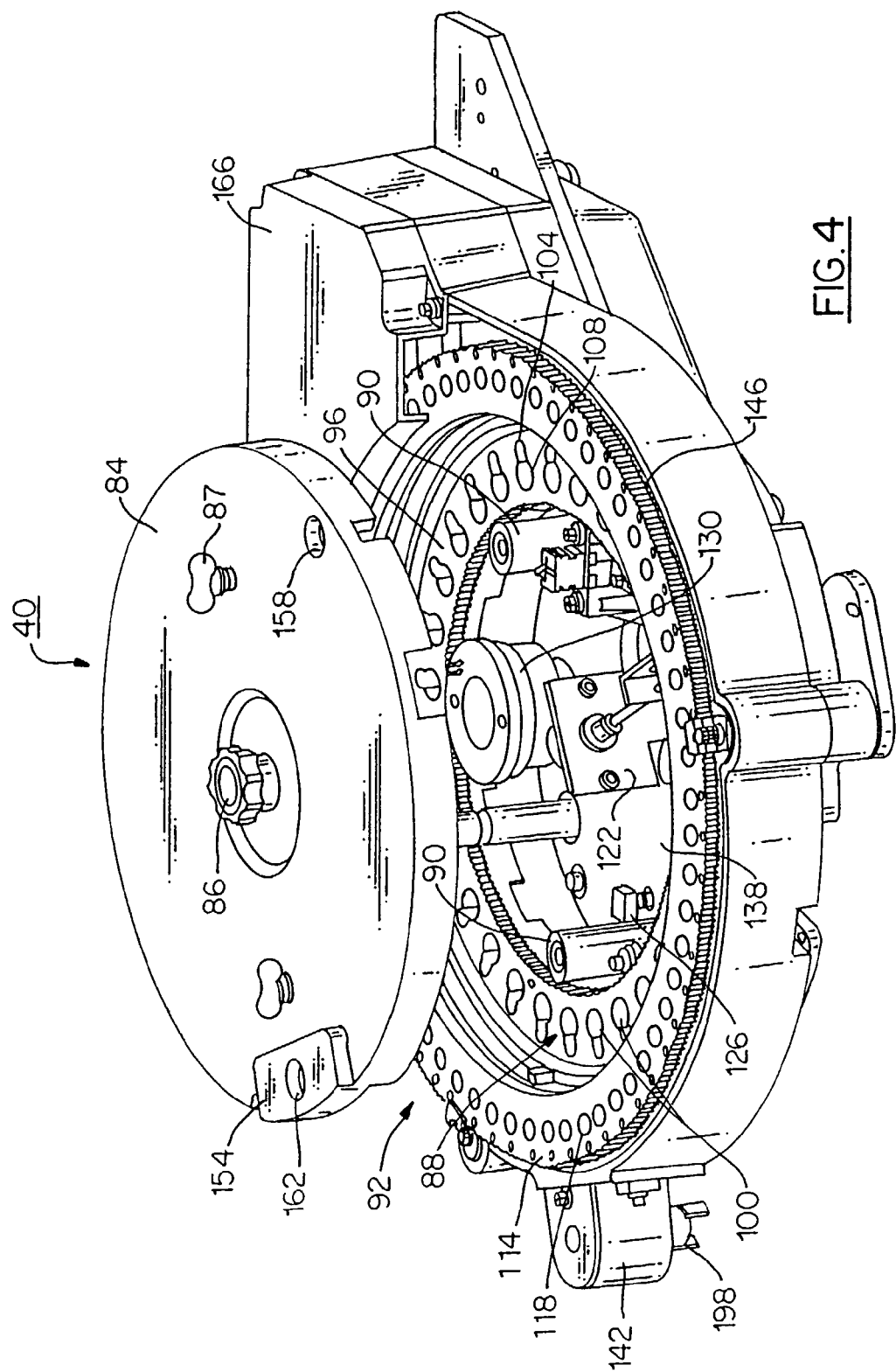
FIG. 4 is the top perspective view of the auxiliary sample handler of FIG. 3, with the cover removed.

Referring to FIGS. 2-4, the auxiliary sample handling apparatus 40 (hereinafter referred to as the auxiliary sample handler) is disposed in spaced relation between the first incubator assembly 34 of the dry chemistry system and the second incubator assembly 56 of the wet chemistry system of the above-described analyzer 10. The auxiliary sample handler 40 includes a circular cylindrical housing 80 having a cover 84. The housing 80 is defined by an interior sized for containing a number of retained components which include an inner rotor assembly 88 (not shown in FIG. 3) a pair of position sensors (only one of which, labeled 126, being shown), and a tip disposal assembly 122. Each of the above-noted components are attached to an interior facing surface of a bottom mounting plate 138 of the housing 80. In addition, an outer rotor assembly 92 is supported at the top of the housing 80, the outer rotor assembly being disposed outside the periphery of the cover 84.

A pair of stanchions 90 also extending from the interior facing surface of the mounting plate 138 assist in supporting the cover 84 which covers the inner rotor assembly 88. The cover 84 further includes a center handle 86, as well as a pair of opposing twist fasteners 87 which engage corresponding openings provided in the stanchions 90. The cover 84 also includes a tip stripping assembly 154 that is described in greater detail below. The following relates to a more detailed discussion of the inner and outer rotor assemblies 88, 92.

Referring to FIGS. 3 and 4, the inner rotor assembly 88 includes a rotatable circular ring member 96, which is rotatably driven about a center axis of rotation by means of a gear drive mechanism. The drive mechanism includes a motor having a rotating engagement portion 130 which extends above the interior facing surface of the mounting plate 138. A set of linear gear teeth are provided on an inner edge of the ring member 96 which mesh with the engagement portion 130. The ring member 96 of the inner rotor assembly 88 further includes a plurality of sample container supply stations 100, each of the stations being circumferentially disposed about the periphery of the ring member. Each of the sample container supply stations 100 are defined by a slotted outer opening 104 which is linked to a radially adjacent and contiguous inner opening 108. The size of the inner opening 108 is much larger than that of the slotted outer opening 104 for reasons which will be become apparent below. According to this specific embodiment, (30) thirty sample container supply stations 100 are provided on the inner ring member 96, though it should be readily apparent that this parameter can be easily varied.

The outer rotor assembly 92 of the auxiliary sample handler 40 extends outside the periphery of the cover 84. This assembly is comprised of a circular support ring 114 having a plurality of circular circumferentially disposed tip supply stations 118 which are equally spaced about the periphery of the ring. Like the inner rotor assembly 88, a gear drive mechanism is used to rotatably drive the ring. A set of linear gear teeth 146 provided on an outer edge of the support ring 114 are engaged by the engagement portion (not shown) of a motor (not shown) to cause rotation of the support ring 114. It should be pointed out that the above described gear drive mechanisms are exemplary. That is, other drive mechanisms can be employed to cause rotational movement of either the support ring 114 or the ring member 96.

The support ring 114 and the ring member 96 of the outer rotor assembly 92 and inner rotor assembly 88, respectively, are concentric, the rotating components of each assembly being independently driven by their respective gear drive mechanisms about a common axis of rotation.

Each of the tip supply stations 118 of the support ring 114 of the outer rotor assembly 92 are circular openings which are sized to receive a metering tip from a tip supply (not shown) at a tip deposit station 150 provided as an opening in an adjacent cover 166 covering the drive motor (not shown) for the rotatable support ring 114 of the outer rotor assembly 92. According to this embodiment, a total of sixty (60) equally spaced tip supply stations 118 are provided, though it should be apparent, as previously noted above, that this parameter can be suitably varied.

According to this specific embodiment, each of the sample container supply stations 100 and the tip supply stations 118 of the inner rotor and outer rotor assemblies 88, 92, respectively, are sized to receive a fluid aspirating/dispensing member. According to this embodiment, the fluid aspirating/dispensing member is a metering tip 102, shown partially in FIG. 6, which includes an open upper end 103 and a lower dispense end 105 through which liquid can be dispensed. More specifically, the metering tip described herein is a disposable plastic member made from polypropylene or other plastic moldable material. More particularly, the metering tip 102, FIG. 6, described herein is manufactured by the Johnson & Johnson Company under the trade name of Vitros™, though it will be apparent that other fluid dispensing/aspirating members can be substituted.

The auxiliary sample handling apparatus 40 further includes a sample integrity read station (not shown) including a station housing into which a metering tip is fed and an optical reading device, such as a spectrophotometer, which includes receiving and transmitting optics disposed on opposite sides of a test slot or cavity. The sample integrity read station is provided to provide spectrophotometric analysis of the sample contents of a sealed metering tip in order to ascertain the presence of certain sera components, such as hemoglobin, albumin, lipoproteins, glucose, and others. Additional details regarding the auxiliary sample handling apparatus 40 are provided in commonly assigned and copending U.S. patent application Ser. No. 09/910,399, entitled: AUXILIARY SAMPLE SUPPLY FOR A CLINICAL ANALYZER, the entire contents of which are herein incorporated by reference.

A tip sealer 142 disposed on the exterior of the housing of the auxiliary sample handler 40 includes a heated element, such as an anvil (not shown), which crimps or permanently seals the dispense end 105 of the metering tip 102, FIGS. 6 and 10. Following the dispensing of sample at the metering station 68, a metering tip 102, FIGS. 6 and 10, containing patient sample is lowered into an opening 182 defined by the tip sealer 142. The sealing of the metering tip 102, FIGS. 6 and 10 permits the tip to become, in effect, a secondary sample container and prevents back splash during ejection of the tip.

Referring to FIG. 2, and with respect to the remaining components of the present analyzer 10, the second incubator assembly 56 is positioned adjacent to the auxiliary sample handling apparatus. The second incubator assembly 56 is sized to receive at least one reaction vessel 64 and includes a read station (not shown) including a testing device, such as a spectrophotometer, for detecting the presence or amount of an analyte in a sample.

Each reaction vessel 64 is conveyed in relation to the second incubator assembly and a metering station for receiving sample from sealed metering tips 102 within the auxiliary sample handling apparatus 40 and at least one reagent from the reagent wheel 52.

The micro-tip supply 60 conveys a plurality of disposable plastic metering tips 107, FIG. 10, in which each of the tips are smaller than the sealed sample-containing metering tips 102, that are retained within the auxiliary sample handling apparatus 40, as shown in FIGS. 3 and 4. The tips 107 are retained in packages which are conveyed to a pickup station which is aligned with the movable truck 44 of the wet chemistry system of the herein described analyzer 10.

Each of the reaction vessels 64 include a plurality of spaced reaction chambers for conducting a wet assay. A preferred version is described in copending and commonly assigned U.S. patent application Ser. No. 09/897,673, entitled: REACTION VESSEL to LaCourt et al, the contents of which are herein incorporated by reference. The cuvettes can be provided for single (disposable) as well as for multiple use, according to the present invention. The vessels 64 of the present embodiment further include windows (not shown) on opposing sides of each reaction chamber which permit testing of the contents by means of a testing device, such as a spectrophotometer (not shown) which is included in a testing chamber which is disposed adjacent to the second incubator assembly 56. It will apparent, however, that other forms of reaction containment devices, such as reaction wells, cuvettes, test tubes, and even thin film or dry slide elements can be substituted.

The rotatable reagent wheel 52 includes a plurality of reagent containers or packs 54 each being disposed within appropriately sized slotted portions of a rotatable ring component. Each of the reagent packs 54 contain at least one and preferably two separately housed reagents within an injection molded structure, the packs being driven by a suitable drive mechanism along a circular path wherein the packs are stored for access and rotated to an appropriate position for aspiration. The reagent packs 54 can be loaded individually through a slot (not shown) in a cover (not shown) of the reagent wheel, the wheel further including a cooler (not shown) which maintains the reagents at an appropriate temperature and humidity. Additional details relating to a suitable reagent management system can be found, for example, in U.S. patent application Ser. No. 09/482,599, previously incorporated in reference herein.

Initially, a plurality of unsealed metering tips 102 are loaded one at a time as fed from a tip supply (not shown) through the opening defining the tip deposit station 150 and are dropped into empty tip supply stations 118 provided on the support ring 114 of the outer rotor assembly 92 of the auxiliary sample handling apparatus 40. The support ring 114 is rotated incrementally by means of the gear drive mechanism (not shown) in order to align empty tip supply stations 118 into proper alignment with the tip deposit station 150.

The movable truck 30 of the primary metering system 22 is shuttled from a "home" position along the transport rail 26 to the auxiliary sample handling apparatus 40 and a metering tip 102, FIG. 6, is picked up by the proboscis of the primary metering mechanism 22 in a commonly known manner. The movable truck 30 is then driven to the primary sample handler 14 and the proboscis and attached metering tip 102, FIGS. 6 and 10, is lowered into an aligned sample container 18. A predetermined volume of patient sample is drawn under vacuum and is aspirated from one of the patient sample containers 18 into the metering tip 102. Specific details relating to the attachment of a metering tip to a proboscis as well as details relating to the aspiration and metering of sample and other fluids are commonly known to those in the field. An additional example is provided, for example, in U.S. Pat. No. 4,340,390 to Collins et al., the entire contents of which are also herein incorporated by reference.

The metering truck 30 carrying the unsealed metering tip 102 with aspirated sample is then shuttled along the transport rail 26 from the primary sample handler 14 to the metering station 68. At the metering station 68, a volumetric portion of patient sample contained within the metering tip 102 is dispensed onto a dry or thin film slide element, shown pictorially as 36 in FIG. 2, which is arranged to be loaded using conventional means, such as a reciprocating pusher blade 39, also shown pictorially in FIG. 2, into the first incubator assembly 34. The sample which is metered is then used in conjunction with the dry chemistry system of the herein described combinational analyzer 10. The sample is metered onto, for example, a clorimetric or potentiometric slide element which is incubated, the sample being analyzed at a read station (not shown) for correlated analyte detection. Details relating generally to the incubation and testing of dry slide elements is known in the field such as described, for example, in U.S. Pat. No. 4,296,069 entitled: Apparatus for Processing an Analysis Slide, and therefore require no further discussion.

Following the above-described metering step, the metering tip 102, shown only in FIG. 6, is further shuttled by the metering truck 30 toward the auxiliary sample handler 40 and more specifically to the tip sealer 142. At the tip sealer 142, the metering tip 102 is placed within an opening 182 and is lowered until the tip is positioned relative to a heating element (not shown). Heat from the heating element is applied through an anvil 198 to the dispense end 105 of the tip 102 while the tip is still attached to the proboscis (not shown) of the metering truck 30. The fluid within the tip 102 is aspirated further away from the dispense end 105 and a bubble is formed which prevents temperature effects to the fluid as well as removing the fluid from the area to be sealed. As noted above, further details relating to the above noted sealing operation are provided in previously incorporated U.S. patent application Ser. No. 09/658,356 entitled: ANALYZER WITH SAMPLE QUALITY MEASUREMENT, AND METHOD.

When the above sealing operation is complete, the sealed metering tip 102 becomes a sample supply container for use by the wet chemistry system of the present combinational analyzer 10 as will be described below.

Following the tip sealing operation, the movable truck 30 of the primary metering mechanism 22 raises the sealed tip 102, FIG. 6, from the tip sealing station 142 and moves into alignment with an opening 162 provided on the cover 84 of the auxiliary sample handler 40. According to the present embodiment, a pair of biased V-blocks (not shown) contacted by a metering tip 102 as it is lowered into the opening are caused to spread apart until the top end 103 of the tip passes between the blocks. Upward movement of the proboscis therefore causes engagement against the shoulder of the open upper end 103 of the metering tip 102, causing the tip to be stripped from the proboscis and dropped vertically into an empty sample container supply position 100 of the circular ring 96 of the inner rotor assembly 88.

The above noted steps are repeated in order that a plurality of sealed metering tips 102 are individually added to the auxiliary sample handler 40 and more specifically to sample container supply stations 100 of the inner rotor assembly 88. The rotatable ring 96 of the inner rotor assembly 88 is driven about its axis of rotation through means of the meshing of the engagement portion 130 of the drive motor and the gear teeth provided on the ring 96 either incrementally or as required. The retained sample containers (sealed metering tips 102) are driven relative to an aspiration station 158 and sample integrity read station (not shown).

The optical reading apparatus provided at the sample integrity read station according to this embodiment, is a spectrophotometer which makes light absorbance transmission measurements of a sample retained within the sealed disposable metering tip 102. The sealed metering tip 102, being made from a transparent plastic material therefore permits optical testing to be performed upon the fluid contents. Details relating to the optical reading of the fluid contents of the sample are known as provided in U.S. Pat. Nos. 6,013,528 and 5,846,492, to Jacobs et al., the entire contents of each being hereby incorporated by reference.

Upon completion of a read, the metering tip 102 is driven into alignment with the opening representing the aspiration station 158. If sample is required, the secondary metering system 42 is used to bring a micro-tip from the micro-tip loader 60 using a proboscis (not shown) extending downwardly from the movable metering truck 44 which is moved into position using the metering transport rail 26. As noted previously, the overall operation of the secondary metering mechanism 42 in terms of the attachment of a tip to the proboscis (not shown), the raising and lowering of the proboscis relative to the metering truck 44, the vertical and longitudinal movement of the metering truck along the transport rail 26 and the aspiration and dispensing of fluid using the micro-tip are literally identical, outside of the size of the reagent probe or proboscis, to that of the primary metering mechanism 22, FIG. 2. As previously defined, however, the micro-tip 107 is a fluid dispensing member which can easily fit within the confines of a sealed metering tip 102, permitting aspiration therefrom.

Figure 9:
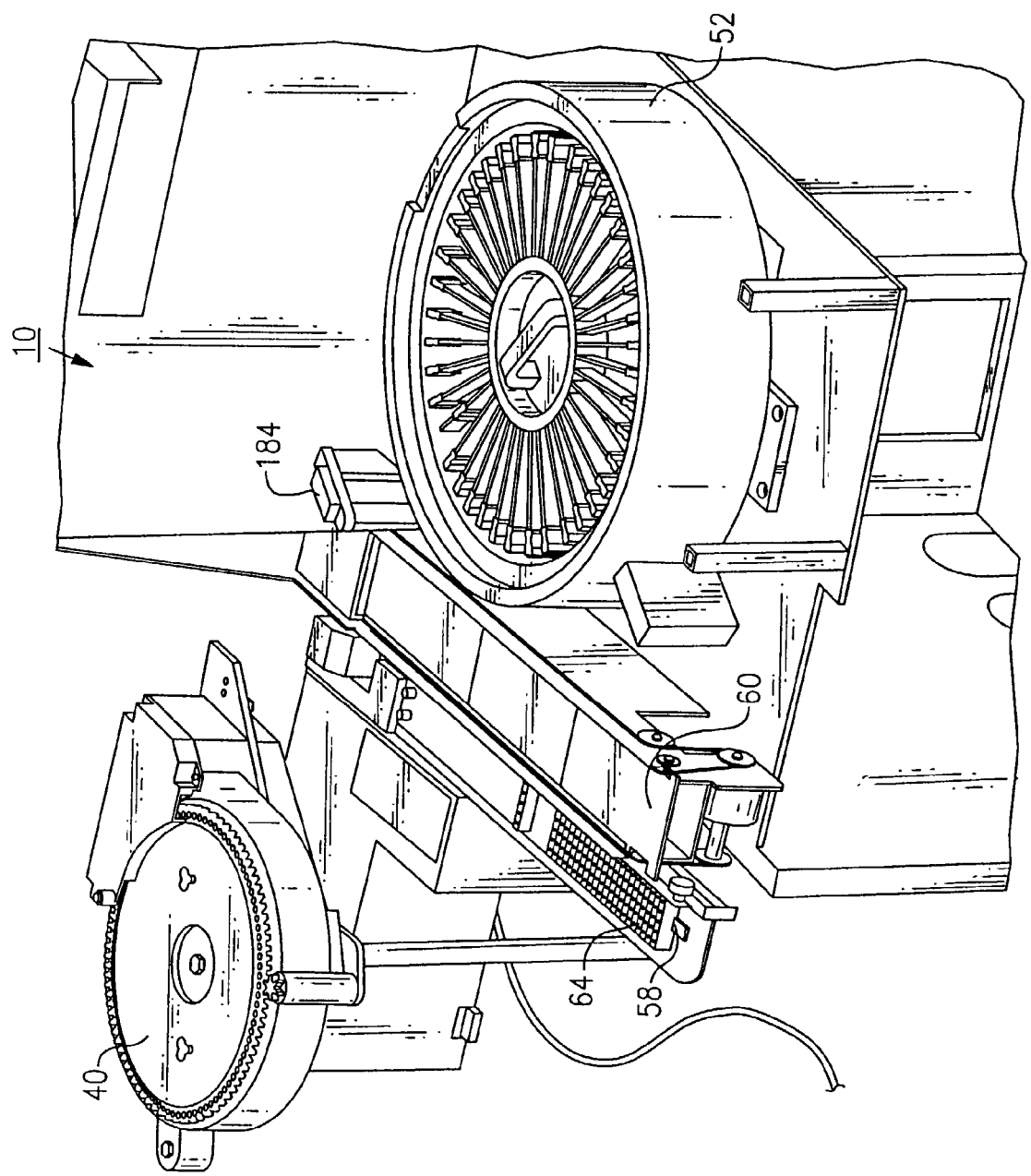
FIG. 9 is a top perspective view of the wet chemistry system of the clinical analyzer of FIG. 2.

The micro-tip 107 is positioned by the movable truck at the aspiration station 158 of the auxiliary sample handling apparatus 40 within the confines of the sealed metering tip 102 in order to aspirate a predetermined volume of liquid from the sealed tip to use the sample as part of a wet assay or dilution. The metering truck 44 then moves the micro tip into alignment with a reaction vessel 64 and lowers the micro-tip 107 into a reaction chamber of the vessel in order to then dispense the aspirated liquid. Following the delivery of patient sample aspirated from the secondary sample container, the micro tip 107 is sealed to prevent back splash of fluid onto the proboscis and is then disposed of by dropping the used micro-tip into a dump station 184, FIG. 9, of the analyzer 10.

As previously noted, the inner opening 108 of the sample container supply stations 100 has a diameter which is larger than that of the upper end 103 of the tapered metering tip 102. Once sample is no longer required from a sealed metering tip, the actuable hook blade can be employed to pull the tip from the slotted outer opening to the larger inner opening, thereby causing the tip to fall through the opening and into a dump station (not shown) located beneath the ring 96. A position sensor (not shown) detects the position of the hook blade relative to the inner rotor assembly 88.

According to a significant part of the present invention, reagents are also brought to the reaction vessel 64 from a reagent container 54 which is rotated to an aspiration position by the reagent wheel 52. According to this embodiment, a mainframe metering tip 102 is first picked up by the movable truck 44 from the outer ring of the auxiliary sample handler apparatus 40 and is then shuttled to the aspiration position of the reagent wheel 52. Reagent fluid is then aspirated from the reagent container 52 into the attached mainframe tip according to this embodiment, or alternatively, one of the micro-tips 107. The used metering tip 102 is then shuttled along the metering rail 26 to the metering position and the reagent is dispensed directly into the reaction chamber of the reaction vessel 64. Preferably, the reaction chamber of the vessel 64 is sized to receive the tip 102, whose dispense end 105 can be positioned within the confines of the reaction vessel and more particularly placed directly into direct contact with the already retained sample/reagent. As reagent is dispensed, the fluids are "swish-mixed", providing an advantage over existing metering systems which require a paddle or other apparatus for mixing.

Following the above dispensing step, this mainframe tip 102 is also sealed and discarded at the dump station 184. Preferably, the coordination of wet assay testing utilizes the auxiliary sample handler 40 as part of the scheduling in order to effectively utilize throughput. Additional quantities of a second reagent and/or sample or other substances such as calibration liquid can be obtained similarly using an unused metering tip 102 or micro-tip 107 which is picked up by the movable truck 44 of the secondary metering system 42 shuttled to an aspiration station for aspiration of an appropriate liquid and then dispensing the liquid into the reaction vessel. As such, there is no need to wash the reagent proboscis since the liquid is retained by the metering tip 102 or micro-tip. Hence, the use of disposable metering tips effectively replaces the wash apparatus normally associated with so-called wet chemistry systems. It should be noted that the sequencing of fluids (sample followed by first reagent followed by second reagent) is not essential relative to the workings of the invention. That is, and in the majority of wet assays, first reagent is first metered into the reaction vessel 64 prior to the dispensing of sample.

Figure 5:
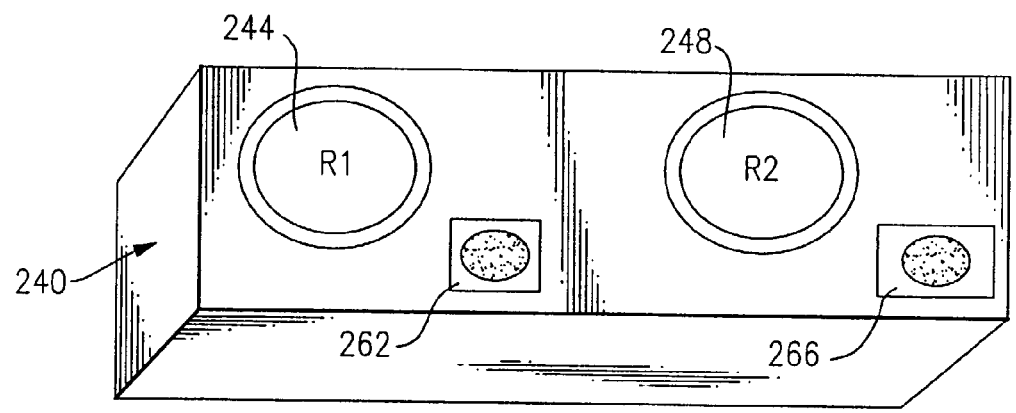
FIG. 5 is a top view of a reagent container made in accordance with a preferred embodiment of the present invention.

Certain modifications and variations are possible within the framework of the inventive concepts as set forth herein. Referring to FIGS. 5 and 6, and in lieu of providing a plurality of separate discrete metering tips for each reagent delivery step, a dedicated metering tip(s) can be used with a reagent container. In this instance, a reagent supply 240 includes a pair of reagent containers 244, 248, each containing a different reagent, labeled R1 and R2. Dedicated metering tips 102, such as those previously described, or other suitable fluid dispensing elements are provided adjacent the mouth of each of the reagent containers 244, 248. In use, the movable truck 44, FIG. 2, is lowered and one of the dedicated metering tips 102 is attached to the reagent probe, depending on whether R1 or R2 is required. The selected reagent is then aspirated from the container 244, 248 using the dedicated metering tip 102. Upon aspirating reagent, the truck is driven to the appropriate metering position of the analyzer and reagent is metered into the reaction vessel 64 in the manner previously described. Following the dispensing of reagent, the movable truck is shuttled back to the reagent supply 240 and the tip 102 is replaced into a corresponding storage receptacle 262, 266.

Figure 7:
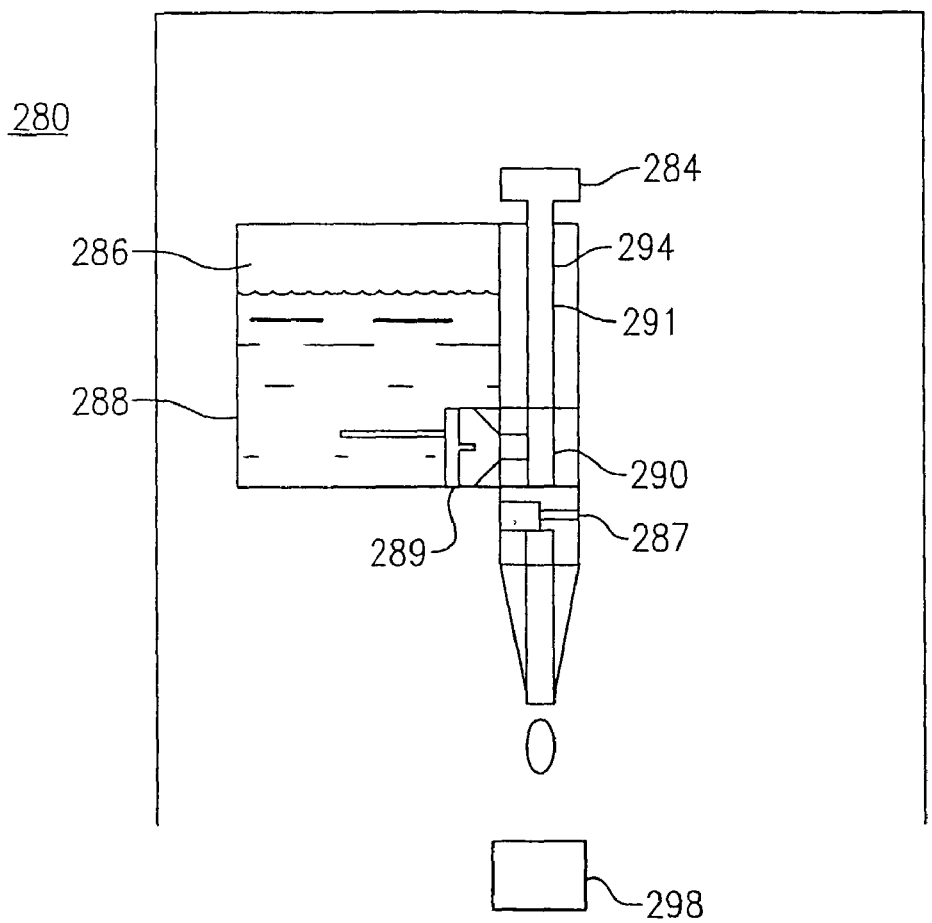
FIG. 7 is a schematic diagram of a self dispensing reagent container made in accordance with a preferred embodiment of the invention.
Figure 8:
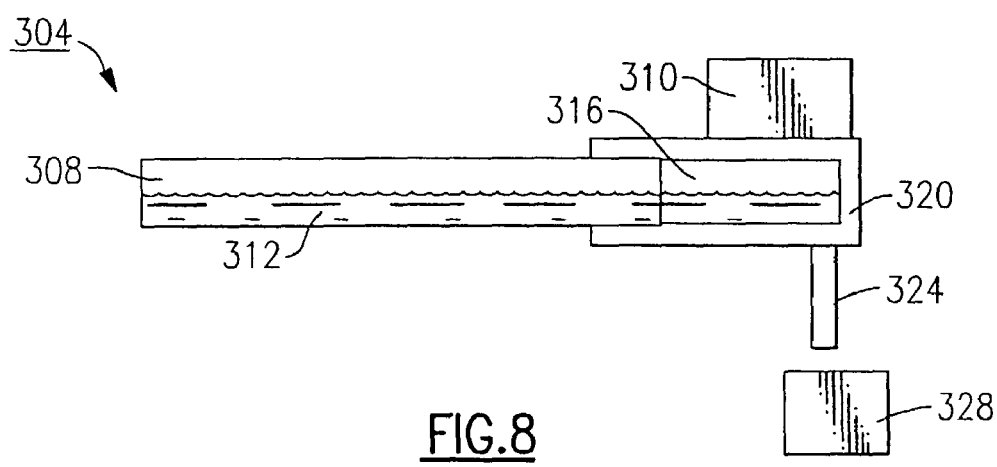
FIG. 8 is a schematic diagram of a self-dispensing reagent container made in accordance with another embodiment of the present invention.

Still other variations are possible to avoid the wash-free operations of the prior art. Referring to FIGS. 7 and 8, a reagent bottle can be provided having self-dispensing means for dispensing a predetermined quantity of reagent without first requiring aspiration of reagent using a disposable or dedicated reagent probe or metering tip.

Referring to FIG. 7, a reagent container 280 includes a defined storage receptacle 286 which includes a quantity of a reagent 288. A pump mechanism 284 capable of dispensing precision micro-volumes of reagent includes a piston 294 provided at the end of a reciprocating drive rod 291 provided in a metering chamber 290. In operation, a portion of the contained reagent 288 is permitted to flow from the receptacle 286 into the adjacent metering chamber 290 by means of a check valve 289 and then aspirate depending on the position of the drive piston 294. Downward movement of the drive rod 291 and piston 294 causes reagent to be metered onto a properly aligned reaction vessel 298 using a separate check valve 287.

Referring to FIG. 8, a second form of self-dispensing mechanism is shown for a reagent supply 304, the supply including a pump mechanism 310 and an actuating member 308 which moves in reciprocating fashion within a cavity 316 of a container housing 320. Movement of the actuating member 308, as shown, and downward stroke of the pump mechanism 310 causes a predetermined volume of reagent 312 to be dispensed to onto a reaction vessel 328 through a vertically disposed outlet 324. The present techniques of FIGS. 7 and 8 preferably utilize a high velocity injection form of metering/mixing versus the swish-mixing employed by the preceding disposable tip metering concepts. It should be readily apparent that other means of dispensing reagent employing the concepts of the present invention can easily be imagined.

| PARTS LIST FOR FIGS. 1-10 | |
| --- | --- |
| 10 | analyzer |
| 14 | primary sample handler |
| 18 | sample containers |
| 22 | primary metering mechanism |
| 23 | sample trays |
| 26 | metering transport rail |
| 30 | metering truck |
| 34 | first incubator assembly |
| 36 | slide element |
| 39 | pusher blade |
| 40 | auxiliary sample handler |
| 42 | secondary metering mechanism |
| 44 | metering truck |
| 52 | reagent wheel |
| 54 | reagent containers |
| 56 | second incubator assembly |
| 58 | reaction vessel conveyor |
| 60 | micro-tip loader |
| 64 | reaction vessel |
| 68 | metering station |
| 80 | housing |
| 84 | cover |
| 86 | handle |
| 87 | twist fasteners |
| 88 | inner rotor assembly |
| 90 | stanchions |
| 92 | outer rotor assembly |
| 96 | circular ring member |
| 100 | sample container supply stations |
| 102 | metering tip |
| 103 | open upper end |
| 104 | outer slotted opening |
| 105 | tapered lower dispense end |
| 107 | micro-tip |
| 108 | inner opening |
| 114 | support ring |
| 118 | tip supply stations |
| 122 | tip removal assembly |
| 126 | position sensor |
| 130 | engagement portion of drive motor |
| 138 | mounting plate |
| 142 | tip sealer |
| 146 | edge teeth -outer ring |
| 150 | tip deposit station |
| 154 | tip stripping assembly |
| 158 | aspiration station |
| 162 | opening |
| 166 | cover |
| 182 | opening |
| 184 | dump station |
| 198 | anvil |
| 200 | reagent probe |
| 210 | wash station |
| 215 | wash cylinder |
| 220 | inlet port |
| 224 | outlet port |
| 240 | reagent supply |
| 244 | reagent container |

| -continued | |
| --- | --- |
| PARTS LIST FOR FIGS. 1-10 | |
| 248 | reagent container |
| 262 | storage receptacle |
| 266 | storage receptacle |
| 280 | reagent container |
| 284 | pump mechanism |
| 286 | storage receptacle |
| 287 | valve |
| 288 | reagent |
| 289 | valve |
| 290 | chamber |
| 291 | drive rod |
| 294 | piston |
| 298 | reaction vessel |
| 304 | reagent container |
| 308 | reciprocating drive member |
| 310 | pump mechanism |
| 312 | reagent |
| 316 | cavity |
| 320 | container housing |
| 324 | outlet |
| 328 | reaction vessel |

It should be readily apparent that only specific exemplary embodiments have been described relating to a number of inventive concepts. Those skilled in the art will readily recognize that numerous changes and modifications can be made without departing from the intended spirit and scope of the invention.

We claim:

1. A wash-free reagent delivery system for introducing a volume of at least one reagent into a reaction containment device in a clinical analyzer, said system including:
   a patient sample supply:
   at least one reagent supply;
   at least one metering system including a metering head movable between said at least one reagent supply and said reaction containment device;
   a first plurality of disposable fluid dispensing tips used to aspirate a volume of reagent from said at least one reagent supply for single-use dispensing into said reaction containment; and
   a second plurality of disposable fluid dispensing tips, each of said second plurality of disposable fluid dispensing tips having a sealed dispense end wherein each of the dispense ends of said second plurality of disposable tips are sealed after a quantity of patient sample is initially aspirated therein using said at least one metering system, thereby forming a container.

2. A clinical analyzer comprising:
   at least one reagent supply;
   a patient sample supply;
   metering system including a metering head that is movable along a metering rail;
   at least one reaction vessel containing a volume of patient sample dispensed from said patient sample supply and a volume of at least one reagent dispensed from said at least one reagent supply; and
   a first plurality of disposable metering tips, said first plurality of disposable metering tips each being used by said metering system to aspirate said volume of at least one reagent from said at least one reagent supply and to dispense said volume into the confines of said at least one reaction vessel wherein each said tip of said first plurality of disposable tips includes a dispense end that is placed by said metering system into said at least one reaction vessel and directly into contact with said volume of patient sample contained therein, said patient sample supply further comprising a second plurality of disposable tips, each of said second plurality of disposable tips containing a quantity of patient sample initially aspirated therein using said metering system, each of said second plurality of disposable tips further including a sealed dispense end, thereby forming a container, said sealed dispense end being formed after initial aspiation of patient sample.

3. An analyzer as recited in claim 2, wherein said reaction vessel is a reaction cuvette.

4. An analyzer as recited in claim 3, wherein said reaction vessel is disposable.

5. A clinical analyzer comprising:
a sample supply including a first plurality of disposable tips, each of said first plurality of disposable tips having a sealed dispense end forming a container and further having a volume of a patient sample fluid initially contained therein;
at least one reagent supply;
at least one reaction containment device for containing a volume of patient sample fluid from said at least one sample supply and a volume of reagent from said at least one reagent supply; and
reagent wash-free delivery means for aspirating said volume of reagent from said at least one reagent supply and dispensing same into said at least one reaction containment device, wherein said wash-free reagent delivery means includes a second plurality of disposable tips, each of said second plurality of disposable tips being attachable to a metering head movable between said second plurality of disposable tips and said at least one reagent supply for aspirating said volume of reagent from said at least one reagent supply and dispensing aspirated reagent into said at least one reaction containment device, said analyzer further including a third plurality of disposable tips for aspirating patient sample fluid from one of said second plurality of disposable sealed tips and aspirating said volume of patient sample fluid into said at least one reaction containment device.

6. A system as recited in claim 1, wherein each of said first plurality of disposable tips are sized to fit within the reaction containment device and to dispense said volume of reagent directly into liquid already contained in said reaction containment device.

7. A system as recited in claim 6, wherein said first plurality of tips are disposed in said patient sample supply.

8. A system as recited in claim 7, wherein said sample supply includes a pair of rotors, each of said rotors being supported for rotational movement and including a plurality of stations wherein said first plurality of tips are disposed in stations in a first of said rotors and said second plurality of sealed tips are disposed in the other of said rotors.

9. A system as recited in claim 6, including a third plurality of disposable tips used to aspirate patient sample from a said sealed disposable tip in said sample supply using said metering system and for dispensing patient sample into said reaction containment device.

10. A system as recited in claim 9, wherein said third plurality of disposable tips are disposed in a supply between said patient sample supply and said at least one reagent supply.

11. An analyzer as recited in claim 2, including a third plurality of disposable tips, each of said third plurality of tips being used to aspirate said volume of patient sample from one of said second plurality of disposable tips in said patient sample supply using said metering system and for dispensing said volume of patient sample into said reaction containment device.

12. An analyzer as recited in claim 11, wherein said third plurality of disposable tips is disposed in a supply between said patient sample supply and said at least one reagent supply.

13. An analyzer as recited in claim 2, wherein said first plurality of disposable tips and said second plurality of disposable tips are each separately disposed on said patient sample supply.

14. An analyzer as recited in claim 11, wherein each of said third plurality of disposable tips are sized to fit within the confines of a said second disposable tip in order to aspirate said volume of patient sample therefrom.

15. An analyzer as recited in claim 11, wherein each of said first plurality of tips are sized to fit within said at least one reaction vessel in order to contact with patient sample already dispensed therein.

16. An analyzer as recited in claim 13, wherein said patient sample supply includes a pair of concentric rotors, a first rotor having a plurality of stations for retaining said first plurality of disposable tips and a second rotor having a plurality of stations for retaining said second plurality of disposable metering tips.

17. An analyzer as recited in claim 16, including a sealing apparatus for sealing the ends of at least one of said pluralities of said first and third disposable tips following dispense of fluid therefrom.

18. An analyzer as recited in claim 17, wherein the sealing apparatus is provided on said patient sample supply.

19. An analyzer as recited in claim 5, wherein said first plurality and said third plurality of disposable tips are each disposed on said sample supply.

20. An analyzer as recited in claim 5, wherein each of said third plurality of disposable tips is sized to permit said tip to be lowered into the confines of a disposable tip from said first plurality of disposable tips to permit patient sample fluid to be aspirated therefrom.

21. An analyzer as recited in claim 5, wherein said sample supply includes a pair of concentric rotors, a first rotor having a plurality of stations for retaining said first plurality of disposable metering tips and a second rotor having a plurality of stations for retaining said second plurality of disposable tips.

22. An analyzer as recited in claim 21, including a sealing apparatus for sealing the ends of at least one of said pluralities of said first and third disposable tips.

23. An analyzer as recited in claim 22, wherein the sealing mechanism is provided on said sample supply.

* * * * *

UNITED STATES PATENT AND TRADEMARK OFFICE
CERTIFICATE OF CORRECTION

PATENT NO.         : 7,250,303 B2                                      Page 1 of 1
APPLICATION NO. : 10/185613
DATED              : July 31, 2007
INVENTOR(S)       : Raymond Francis Jakubowicz et al.

It is certified that error appears in the above-identified patent and that said Letters Patent is hereby corrected as shown below:

Col. 17, line 9, please delete the words "after initial aspiration" and replace with --after initial aspiration--;

Signed and Sealed this

Thirtieth Day of October, 2007

JON W. DUDAS
*Director of the United States Patent and Trademark Office*